United States Patent [19]

Bartlett

[11] Patent Number: 5,128,189
[45] Date of Patent: Jul. 7, 1992

[54] DISPOSABLE MAT WITH COMPRESSIBLE RIDGE

[76] Inventor: David H. Bartlett, 1422 W. Skyline Dr., Madison, Wis. 53705

[21] Appl. No.: 395,892

[22] Filed: Aug. 18, 1989

[51] Int. Cl.[5] .............................................. B32B 3/26
[52] U.S. Cl. ...................................... 428/71; 184/106; 296/38; 428/81; 428/157; 428/191; 428/192
[58] Field of Search ........................... 184/106; 296/38; 428/71, 74, 76, 81, 84, 157, 191, 192, 77, 78, 83

[56] References Cited

U.S. PATENT DOCUMENTS 4,671,024 6/1987 Schumacher ..................... 184/106
4,798,754 1/1989 Tomek ............................... 428/157

*Primary Examiner*—William J. Van Balen
*Attorney, Agent, or Firm*—Stroud, Stroud, Willink, Thompson & Howard

[57] ABSTRACT

The invention described and claimed in the present application is of a disposable mat for protecting floors or other surfaces against spillage or droppage of liquid substances. The mat has a top absorbent layer, a bottom liquid impervious layer and a compressible ridge about the periphery. The compressible ridge of the mat of the invention acts as an containment dam for non-absorbent liquid. The ridge is sufficiently compressible to permit equipment on rollers to be moved across the mat.

9 Claims, 2 Drawing Sheets

DISPOSABLE MAT WITH COMPRESSIBLE RIDGE

FIELD OF USE

This invention relates generally to disposable mats for protecting floors and other surfaces. More particularly, it relates to disposable mats for use in areas where there is a tendency toward sudden spillage or droppage of liquids such as operating rooms o chemistry laboratories.

BACKGROUND OF THE INVENTION

Operating rooms generally, and suites for arthroscopic surgical procedures specifically, are areas where spillage of large amounts of liquid or fluid material is a common occurrence. In the case of arthroscopic surgical procedures, large quantities of saline solution are used to irrigate the joint. Also fluid from the wound itself may have to be evacuated. Often these liquids are spilled onto the floor of the operating room. Ordinary absorbent mats can handle gradual seepage of liquid, but if large amounts are spilled at one time, the liquid will spill off the edges of the mat before it ca be absorbed.

Such spillage of liquid on the operating room floor can create a hazard of slippage for the medical personnel, and it can also create a problem with the sanitary conditions of the surgical suite.

In years past such spills have been cleaned by the maintenance personnel following the surgical procedure. The traditional methods have involved mopping or soaking up liquids, and/or collecting or gathering solids. Such clean-up often involves cleaning up bodily fluids which can contain pathogens such as the AIDS virus or the hepatitis virus. Thus, contact between the cleaning person and the substances spilled is often undesirable, yet unavoidable and presents such personnel with a risk of infection.

More recently, out-patient surgery has become an attractive alternative for a number of conditions, particularly arthroscopic surgery. In order to make out-patient surgery cost efficient, it is necessary to reduce the amount of cleanup and thus the amount of time between surgical procedures. A number of products have been developed to reduce the cleanup time between procedures and also alleviate the hazard created by spillage during the procedure. For example, U.S. Pat. No. 4,679,590 to Hergenroeder describes and claims a receptacle device for collecting fluid spilled in a surgical suite. The device is made of molded rubber or a similar synthetic and contains channels which carry the fluid away. Although perhaps an effective way to control the hazard of slippage created by spilled fluids, the device is quite complicated, is not disposable and so must itself be periodically cleaned and disinfected. The present invention provides an inexpensive yet effective alternative to a device such as that described in the '590 patent. Further, the present invention is for a disposable mat so the dangers and problems of cleaning the mat itself are now avoided.

SUMMARY OF THE INVENTION

The present invention is a disposable mat for protecting floors or other surfaces against spillage or droppage of liquid substances. The disposable mat of the invention is comprised of a sheet having a top absorbent layer made of a cellulose-like material and a bottom, non-absorbent, liquid-impervious layer made of a polyethylene-like material. A releasable adhesive is applied to the bottom surface of the bottom layer so that when the mat is laid upon the surface to be protected, it will releasably adhere to that surface. About the periphery of the sheet is formed a compressible ridge made of an open-celled foam material. In use, the ridge acts as a containment wall or dam for non-absorbed liquid. The ridge is sufficiently compressible, however, to permit equipment on rollers to be moved across the mat.

In one embodiment of the mat, the compressible ridge is formed by attaching to the bottom surface of the mat a strip of open-celled foam material. This foam material is positioned so that when the mat is laid upon the surface to be protected, the sheet drapes over the foam strip forming a compressible ridge.

In another embodiment of the mat, the open-celled foam material is laminated between the layers of the sheet and positioned so that when the mat is laid upon the surface to be protected, a compressible ridge is formed about the periphery of the mat. These and other specific features of the invention can be better understood from the detailed description that follows.

DESCRIPTION OF THE PREFERRED EMBODIMENTS

Figure 1:
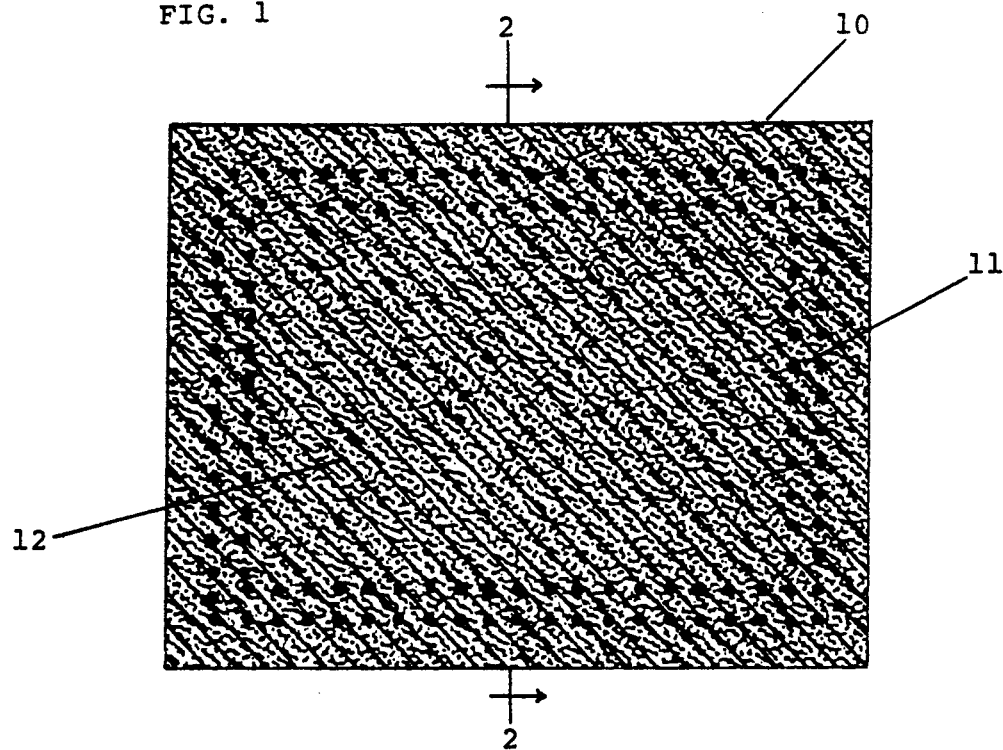
FIG. 1 a top plan view of the disposable mat of the present invention.
Figure 2:
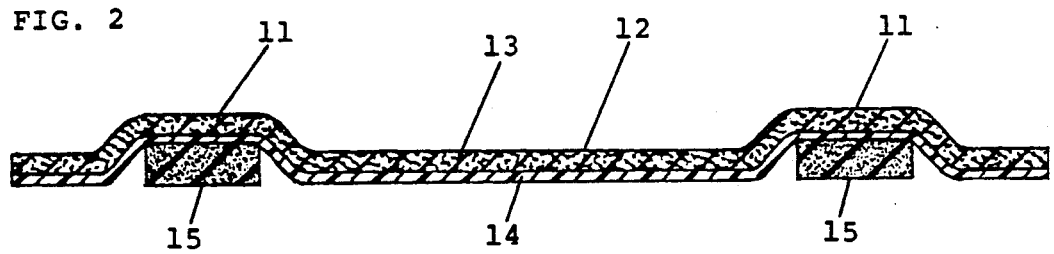
FIG. 2 is a cross section on line 2—2 of FIG. 1.

Referring now to the drawings, FIG. 1 is a top plan view of the disposable mat 10 of the invention showing the compressible ridge 11 about the periphery of the mat. The mat of FIG. 1. is illustrated as a generally rectangular shape. It should be understood that the shape of the mat is not important to the essence of the invention. The mat could as easily be assembled in a circular shape, in the shape of a runner or any regular or irregular shape, provided the compressible ridge was formed about the periphery of the mat. In FIG. 2 a cross section of one embodiment of the mat is illustrated. As can be seen in this embodiment, the mat is comprised of a laminated sheet material having a top layer and a bottom layer. The top layer of the disposable mat of the invention is formed of an absorbent material and in the preferred embodiment is formed of an air lay non-woven paper fiber manufactured by the Fort Howard Paper Company of Green Bay WI. In practice the absorbent material can be of a cellulose or cellulose-like material. Examples include either embossed or smooth web material using wood pulp, rayon or a combination, bonded with latex or other binding materials. This material may also include additives, such as starch or polypropylene, to improve absorbency or strength.

The bottom layer 14 of the sheet of the preferred embodiment is a non-absorbent fluid impervious film. This film is laminated to the absorbent layer(s) of the sheet and is formed of a polyethylene or polyethylene-like material. Examples include, polyvinylchloride (PVC), urethanes, polyesters, latex or rubber-based materials, polyethers or combinations of the above. In the preferred embodiment, a ½ml. thick polyethylene film manufactured by Tufco of Green Bay, WI, is laminated to the absorbent layer using a spray acrylic adhesive.

Figure 3:
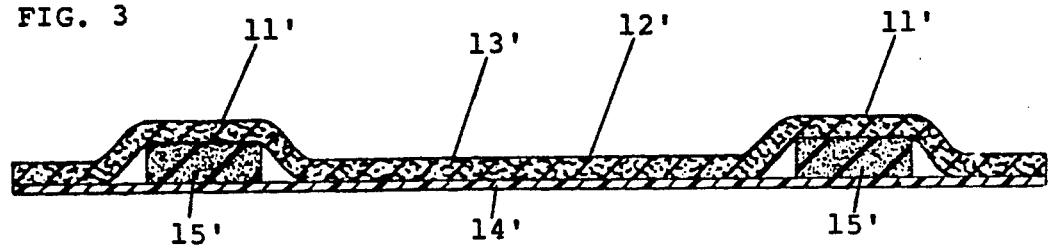
FIG. 3 is a cross section of an alternative embodiment of the invention on line 2—2 of FIG. 1.
Figure 5:
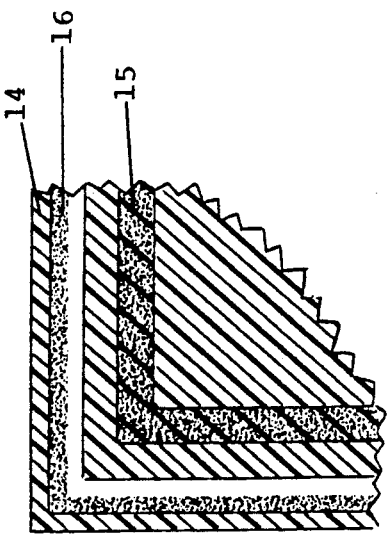
FIG. 5 is a partial view of the bottom surface of one embodiment of the invention.

FIG. 2 illustrates that the compressible ridge of the invention is formed by adhering a strip of open-celled foam material 15 to the bottom surface of the sheet. As can be readily understood by reference to FIG. 2 and FIG. 5, the open-celled foam material 15 is a strip of such material positioned a sufficient distance in from the edge of the sheet such that when the sheet is placed on the floor or other surface, the sheet material 17 drapes over the open-celled foam material forming a compressible ridge. In the preferred embodiment, the open-celled foam material is formed of a polyurethane strip which is longer and wider than it is deep. Suitable material for this use is that obtained from Illbruck Co., Washington Avenue North, Minneapolis, Minnesota, and sold under the ID number R200V. This product comes with an adhesive applied to one surface of the foam material. A protective paper strip is placed over the adhesive. This protective strip is removed and the foam strip is adhered to the sheet at a sufficient distance from the edge of the sheet (as illustrated in FIG. 5) so that when the mat is placed on the floor, the sheet will properly drop over the foam forming a compressible ridge. Other examples of suitable material for the open-celled foam strip include weather stripping, gasket stripping, or any pliable material such as foam, rubber, plastic or extruded material. FIG. 3 illustrates an alternative embodiment of the invention wherein the open-celled foam material 15' is laminated between the absorbent layer 13' and the non-absorbent layer 14'. In practice, the disposable mat of the invention is laid over the surface to be protected. In the preferred embodiment, the mat is releasably adhered to the floor or surface to be protected by applying a non-hygroscopic, releasable, pressure-sensitive adhesive to at least a portion of the bottom surface of the bottom layer 14. In the preferred embodiment, a double backed acrylic adhesive strip with carrier 16 is applied at the outside edge of the bottom surface of the sheet 14 as illustrated in FIG. 5 which is a partial view of the bottom of the embodiment of FIG. 2. Bethem Manufacturing of Lincoln Blvd., Middlesex, NJ, produces a suitable double-backed adhesive strip for this purpose and sells the adhesive strip with a protective liner under the trade name STICKY-T. Other suitable adhesives for this purpose are Avery K-6 and K-7 adhesives manufactured by Avery Label Company and marketed under the trademark KUM KLEEN. The use of a releasable adhesive on some portion of the bottom surface of the bottom layer and particularly the outside edge of the bottom surface safeguards against slippage and tripping over the edge of the mat. The use of a releasable adhesive on the outside edge, as illustrated in FIG. 5, also facilitates proper draping of the sheet Over the foam material 15 so that a compressible ridge is formed.

With the mat releasably adhered to the surface or floor to be protected, the open-celled foam material will create a slight ridge about the periphery of the mat. This ridge acts as a containment dam for excess fluid that is not readily absorbed by the absorbent layer of the mat. The type of situation for which the mat of the present invention is particularly useful is where a large amount of liquid is spilled onto the mat at a rate faster than can be absorbed by the absorbent layer of the mat. With the ordinary mat, non-absorbed fluid would overflow the edges of the mat and soil the surface or the floor to be protected. With the mat of the present invention, however, non-absorbed fluid is contained within the boundaries of the ridge.

Figure 4A:
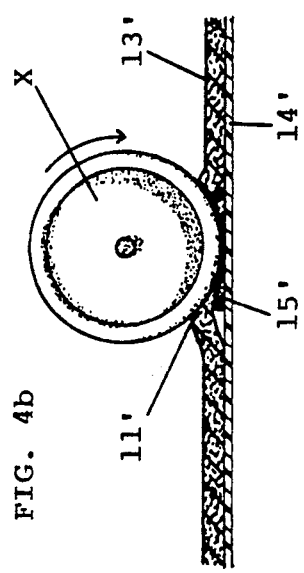
FIG. 4a–4d is a cross section illustrating the compressible feature of the ridge.
Figure 4B:
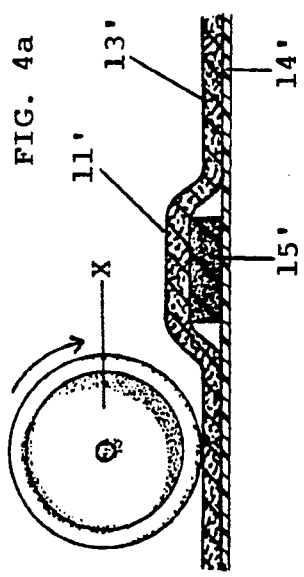
Figure 4C:
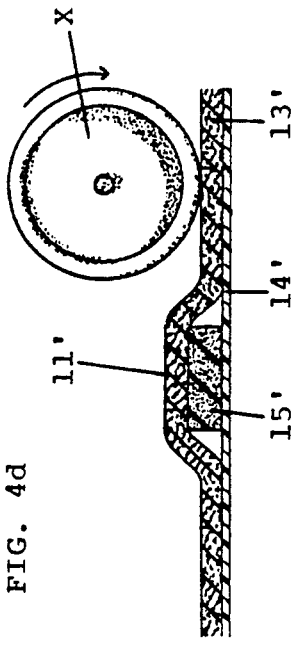
Figure 4D:
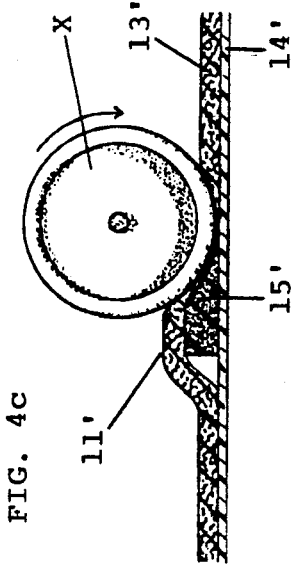

At the same time, if it is necessary to move equipment on rollers (e.g. IV stands, medical equipment, etc.) across the mat, this can be readily done as is illustrated in FIGS. 4a–4d. In FIG. 4a the roller X approaches the ridge 11' In FIGS. 4b and 4c it can be seen that the weight of the roller X compresses the ridge 11' as it moves over the ridge 11' In FIG. 4d it can be seen that after the roller X moves over the ridge 11', the foam material 15' returns to normal and the ridge 11' is restored.

As indicated earlier, the disposable mat of the invention has particular utility for protecting the floor of an arthroscopic operating room. The mat of the invention would be equally useful as a runner in the entrance way of a building or in a laboratory where there is a tendency toward droppage or spillage of liquids. The mat may also be made in a size suitable for countertops such as in a laboratory setting.

While the preferred embodiment of the invention has been described in detail, it will be apparent that modifications and alterations may be made therein without departing from the spirit and scope of the invention set forth in the appended claims.

What is claimed is:

1. A disposable mat for protecting a floor or other surface against spillage or droppage of liquid substances, comprising:
   (a) a laminated sheet having a top absorbent layer and a bottom, nonabsorbent, liquid impervious layer;
   (b) means for forming about the periphery of said sheet, a compressible ridge, said ridge being sufficiently rigid so as to act as a containment barrier to nonabsorbed liquid, but said ridge being sufficiently compressible so as to permit easy movement across said mat of equipment on rollers, said means for forming said compressible ridge including applying to the bottom surface of said sheet a strip of open celled foam material, said foam material positioned such that when said sheet is placed on the floor or other surface, said sheet drapes over said foam material forming a compressible ridge about the periphery of said sheet.

2. A disposable mat as claimed in claim 1, wherein said foam material is formed of a polyurethane-like open-celled foam.

3. A disposable mat as claimed in claim 1, wherein said means for forming said compressible ridge includes laminating between said top layer and said bottom layer a strip of open-celled foam material, said foam material positioned between said layers such that when said sheet is placed on said floor or other surface, a compressible ridge is formed about the periphery of said sheet.

4. A disposable mat as claimed in claim 3, wherein said foam material is formed of a polyurethane-like open-celled foam.

5. A disposable mat for a protecting a floor or other surface against spillage or droppage of liquid substances, comprising:
   a. a laminated sheet having a top absorbent layer formed of cellulose-like material and a bottom, non-absorbent, liquid impervious layer formed of a polyethylene-like film;

b. a compressible ridge about the periphery of said sheet, said compressible ridge formed of polyurethane-like open celled foam material, said ridge being sufficiently rigid so as to act as a containment barrier to non-absorbed liquid, but said ridge being sufficiently compressible so as to permit easy movement across said mat of equipment on rollers.

6. A disposable mat for protecting a floor or other surface against spillage or droppage of liquid substances, comprising:
   (a) a laminated sheet having a top absorbent layer and a bottom, nonabsorbent, liquid impervious layer;
   (b) means for forming about the periphery of said sheet a compressible ridge, said ridge being sufficiently rigid so as to act as a containment barrier to nonabsorbed liquid, but said ridge being sufficiently compressible so as to permit easy movement across said mat of equipment on rollers, said means for forming said compressible ridge including applying to the bottom surface of said sheet a strip of open celled foam material, forming a compressible ridge about the periphery of said sheet; and
   (c) means for releasably adhering said sheet to said floor or other surface.

7. A disposable mat as claimed in claim 6, wherein said foam material is formed of a polyurethane-like open-celled foam 8. A disposable mat as claimed in claim 7, wherein said means for forming said compressible ridge includes laminating between said top layer and said bottom layer a strip of open-celled foam material, said foam material positioned between said layers such that when said sheet is placed on said floor or other surface, a compressible ridge is formed about the periphery of said sheet.

9. A disposable mat as claimed in claim 8, wherein said foam material is formed of a polyurethane-like open-celled foam.

* * * * *